US012575925B2

(12) United States Patent
Valle et al.

(10) Patent No.: US 12,575,925 B2
(45) Date of Patent: Mar. 17, 2026

(54) INTRAOCULAR LENS INJECTOR APPARATUS

(71) Applicant: Bausch + Lomb Ireland Limited, Dublin (IE)

(72) Inventors: Moises Valle, Tustin, CA (US); Sushant Muchhala, Grand Prairie, TX (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 684 days.

(21) Appl. No.: 18/053,070

(22) Filed: Nov. 7, 2022

(65) Prior Publication Data

US 2024/0148492 A1     May 9, 2024

(51) Int. Cl.
A61F 2/16     (2006.01)

(52) U.S. Cl.
CPC ...... A61F 2/167 (2013.01); *A61F 2002/1681* (2013.01)

(58) Field of Classification Search
CPC . A61F 2/167; A61F 2002/1681; A61F 2/1678
See application file for complete search history.

(56) References Cited

U.S. PATENT DOCUMENTS

| | | | |
|---|---|---|---|
| 4,919,130 A | | 4/1990 | Stoy et al. |
| 5,735,858 A | * | 4/1998 | Makker ................... A61F 2/167 |
| | | | 606/107 |
| 5,772,666 A | | 6/1998 | Feingold et al. |
| 5,776,138 A | | 7/1998 | Vidal et al. |
| 5,868,752 A | | 2/1999 | Makker et al. |
| 6,162,229 A | | 12/2000 | Feingold et al. |
| 6,334,462 B1 | | 1/2002 | Dore et al. |
| 6,447,520 B1 | * | 9/2002 | Ott ........................ A61F 2/1678 |
| | | | 606/107 |
| 6,800,076 B2 | | 10/2004 | Humayun |
| 6,923,815 B2 | | 8/2005 | Brady et al. |
| 8,858,625 B2 | | 10/2014 | Putallaz et al. |
| 9,155,615 B2 | | 10/2015 | Valle et al. |
| 9,237,947 B2 | | 1/2016 | Valle |
| 9,662,200 B2 | | 5/2017 | Muchhala et al. |
| 9,931,242 B2 | | 4/2018 | Biddle et al. |
| 10,722,346 B2 | | 7/2020 | Valle et al. |

(Continued)

FOREIGN PATENT DOCUMENTS

| | | |
|---|---|---|
| DE | 102020125130 B | 1/2022 |
| EP | 3 834 775 A | 6/2021 |

(Continued)

*Primary Examiner* — Julian W Woo
(74) *Attorney, Agent, or Firm* — Simpson & Simpson, PLLC; Jeffrey B. Powers

(57) ABSTRACT

An injector for injecting an IOL into an eye, comprising an injector body having a lumen wall defining a lumen, a plunger having a longitudinal axis and a soft tip at a distal end of the plunger. The soft tip having a concave distal surface. In a plane including the longitudinal axis, the plane being perpendicular to an IOL optical axis when the IOL is located at a staging area of the injector body, the concave distal surface extending in a direction at a non-perpendicular angle relative to the longitudinal axis. The concave distal surface may be oval-shaped in a plane perpendicular to the direction, and the concave distal surface has no curvature along the direction.

18 Claims, 17 Drawing Sheets

(56)                    References Cited

U.S. PATENT DOCUMENTS

| | | | |
|---|---|---|---|
| 11,045,310 B2 | 6/2021 | Glick | |
| 11,076,949 B2 | 8/2021 | Germann et al. | |
| 11,278,395 B2 | 3/2022 | Valle et al. | |
| 2001/0007075 A1 | 7/2001 | Hjertman et al. | |
| 2002/0193805 A1 | 12/2002 | Ott et al. | |
| 2004/0111094 A1* | 6/2004 | Meyer | A61F 2/1664 |
| | | | 606/107 |
| 2005/0065534 A1 | 3/2005 | Hohl | |
| 2007/0005135 A1 | 1/2007 | Makker et al. | |
| 2007/0173860 A1 | 7/2007 | Iwasaki | |
| 2008/0027461 A1 | 1/2008 | Vaquero et al. | |
| 2010/0121340 A1* | 5/2010 | Downer | A61F 2/167 |
| | | | 606/107 |
| 2010/0125278 A1 | 5/2010 | Wagner | |
| 2012/0289969 A1 | 11/2012 | Seyboth et al. | |
| 2020/0054487 A1 | 2/2020 | Ross et al. | |
| 2021/0007841 A1 | 1/2021 | Zielke | |
| 2021/0093447 A1 | 4/2021 | Heckler et al. | |

FOREIGN PATENT DOCUMENTS

| | | |
|---|---|---|
| JP | 2008 006137 | 1/2008 |
| WO | 97/26844 A2 | 7/1997 |
| WO | 2015075489 A2 | 5/2015 |
| WO | 2020186365 A1 | 9/2020 |

* cited by examiner

INTRAOCULAR LENS INJECTOR APPARATUS

FIELD

Injector apparatus and methods to control the folding of an intraocular lens for insertion into an eye.

BACKGROUND

Intraocular lenses (referred to herein as IOLs or, simply, lenses) are artificial lenses used to replace natural crystalline lenses of patients when their natural lenses are diseased or an eye is otherwise impaired. Under some circumstances a natural lens may remain in a patient's eye together with an implanted IOL. IOLs may be placed in either the posterior chamber or the anterior chamber of an eye.

IOLs come in a variety of configurations and materials. Various instruments and methods for implanting such IOLs in an eye are known. Typically, an incision is made in a patient's cornea and an IOL is inserted into the eye through the incision. In one technique, a surgeon uses surgical forceps to grasp the IOL and insert it through the incision into the eye. While this technique is still practiced today, more and more surgeons are using IOL injectors, which offer advantages such as affording a surgeon more control when inserting an IOL into an eye and permitting insertion of IOLs through smaller incisions. Relatively small incision sizes (e.g., less than about 3 mm) are preferred over relatively large incisions (e.g., about 3.2 to 5+mm) since smaller incisions have been attributed with reduced post-surgical healing time and reduced complications such as induced astigmatism.

For an IOL to fit through a small incision, it is typically folded and/or compressed prior to entering the eye where it assumes its original unfolded/uncompressed shape. Since IOLs are very small and delicate articles of manufacture, great care is taken in their handling, both as they are loaded into an injector and as the lenses are injected into patients' eyes.

It is desirable that an IOL be expelled from the tip of the IOL injector and into an eye in an undamaged condition and in a predictable orientation. Should an IOL be damaged or expelled from the injector in an incorrect orientation, a surgeon may need to remove or further manipulate the IOL in the eye, possibly resulting in trauma to the surrounding tissues of the eye. To achieve proper delivery of an IOL, it is desirable to have consistent loading of the IOL into the injector device, consistent engagement of the lens by the plunger tip and controlled movement of the lens through the injector lumen and into an eye all with a limited opportunity for misalignment or damaging of the IOL.

Various IOL injectors and other devices have been proposed and produced which attempt to address issues related to ejecting IOLs into an eye, yet there remains a need for IOL injectors and injector components that facilitate surgical delivery of an IOL into an eye.

SUMMARY

According to aspects of the present invention, an IOL injector comprises a plunger having a longitudinal axis and a soft tip at a distal end of the plunger. The soft tip is positioned to advance the IOL through a lumen of the injector and into an eye. The soft tip has a concave distal surface. In a plane including the longitudinal axis, the plane being perpendicular to an IOL optical axis when the IOL is located at a staging area of the injector body, the concave distal surface extends non-perpendicularly to the longitudinal axis. By angling the concave distal surface in such a manner, contact between the concave distal surface and the IOL haptic is controlled and the haptic is reliable positioned onto top of the optic body of the IOL prior to and during folding and compression of the IOL as the IOL travels down the IOL lumen.

An aspect of the present invention is directed to an injector for injecting an IOL into an eye. The injector comprises an injector body having a lumen wall defining a lumen, the IOL to be delivered into the eye at the distal end of the lumen. The injector also comprises a plunger having a longitudinal axis and a soft tip at a distal end of the plunger. The soft tip is positioned to advance the IOL through the lumen to the distal end of the lumen. The soft tip has a concave distal surface. In a plane including the longitudinal axis, the plane is perpendicular to an IOL optical axis when the IOL is located at a staging area of the injector body, and the concave distal surface extends in a direction at a non-perpendicular angle relative to the longitudinal axis.

In some embodiments, the concave distal surface is oval-shaped in a plane perpendicular to the direction, and the concave distal surface has no curvature along the direction. In some embodiments, the concave distal surface is cylindrically shaped in a plane perpendicular to the direction, and the concave distal surface has no curvature along the direction.

The soft tip may comprise an elastomer.

In some embodiments, the concave distal surface defines a concavity, and no feature of the soft tip extends into the concavity. In some embodiments, the concave distal surface has a blind bore formed therethrough, the blind bore extending through the soft tip proximally from the concave distal surface.

The angle of the concave distal surface extends relative to the longitudinal axis may be in the range of 40-70 degrees. The angle of the concave distal surface extends relative to the longitudinal axis may be in the range of 45-65 degrees. In some embodiments, the angle is about 60 degrees.

In some embodiments, the injector may have an intraocular lens (IOL) disposed in a staging area of the injector body, the IOL having a haptic extending proximally from the optic, the soft tip configured to contact less than 10% of the haptic length at initial contact between the soft tip and the haptic, where the haptic length is measured from a circumferential edge of the optic body to a distant end of the haptic. In some embodiments, the soft tip is configured to contact no more than 50% of the haptic length at any point during the plunger actuation.

The injector body may be comprised of two or more components each forming a portion of the lumen. In some embodiments, at least one of the components constitutes an IOL shuttle.

In some embodiments, the shuttle has an IOL disposed therein in a biased state with a center of optic body displaced slightly downward relative to opposing circumferential outer edge locations of the optic body.

In some embodiments, the injector body comprises finger flanges and the plunger comprises a thumb press.

Another aspect of the invention is directed to a plunger for use in an IOL injector. The plunger comprises a shaft having a longitudinal axis, and a soft tip at a distal end of the shaft. The soft tip has a concave surface extending along a direction, the direction forming a non-perpendicular angle with the longitudinal axis. In some embodiments, the plunger is in a combination with an injector body having a lumen, the plunger disposed to slide within the lumen.

Yet another aspect of the invention is directed to a method of inserting an intraocular lens (IOL) including an optic body and a haptic into an eye through a lumen of an injector. The injector comprises a plunger including i.) a shaft characterized by a longitudinal axis and ii.) a soft tip at a distal end of the shaft. The soft tip has a concave distal surface extending along a direction, the direction forming a non-perpendicular angle with the longitudinal axis. The method comprises actuating the plunger to move a portion of the haptic on top of the optic body using the concave distal surface.

In some instances, the actuating step comprises, upon initial contact with the haptic, contacting less than 10% of the haptic length as measured from the optic body to a distant end of the haptic.

In some instances, the actuating step comprises, moving the IOL from a staging area of the injector body through a distal end of the lumen while contacting no more than 50% of the haptic length at any point during movement of the IOL from the staging area to the distal end of the lumen.

The concave distal surface may be oval-shaped in a plane perpendicular to the direction, and the concave distal surface has no curvature along the direction.

The term "distal" refers to components or portions of an injector, IOL or other device that are nearer to the end of the injector where an IOL exits the injector into an eye; and the term "proximal" refers to components or portions of an injector or other device that are further from the end of the injector where an IOL exits the injector into an eye.

These and other aspects of the present invention will become apparent upon a review of the following detailed description and the claims appended thereto.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Aspects of the invention will be further described with reference to the following specific examples. It is understood that these examples are given by way of illustration and are not meant to limit the scope of the claimed invention beyond the text of the claims set forth below.

Figure 1:
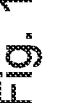
FIG. 1 is a schematic illustration of an example of an assembled injector system according to aspects of the present invention.
Figure 2:
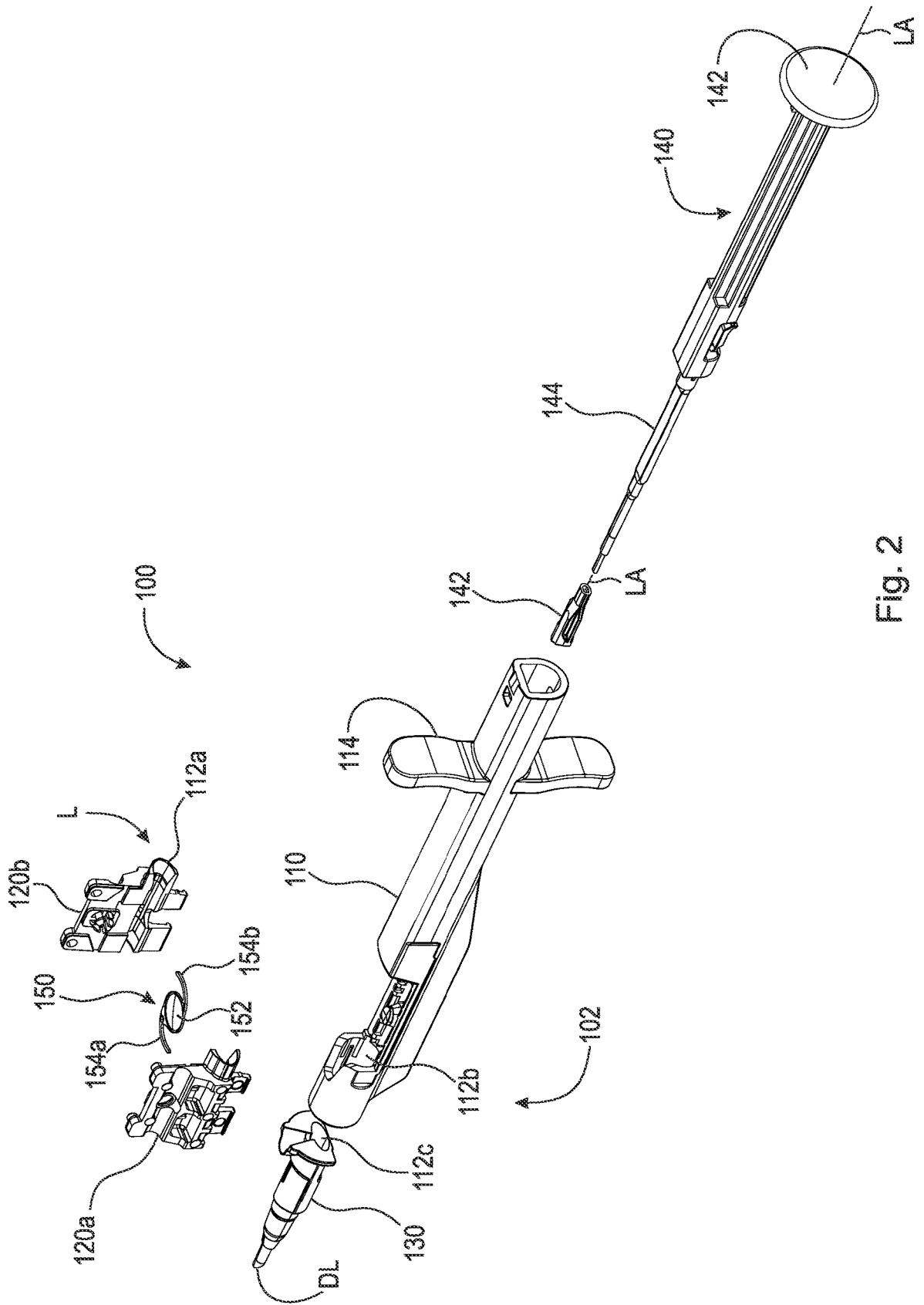
FIG. 2 is a schematic illustration of the example of FIG. 1 in a disassembled state.

FIG. 1 is a schematic illustration of an example of an assembled injector system 100 for injecting an IOL 150 into an eye (shown in FIG. 2), according to aspects of the present invention; and FIG. 2 is a schematic illustration of injector system 100 shown in a disassembled state, to facilitate discussion.

Injector system 100 comprises and injector body 102 and a plunger 140. The injector body has a lumen wall 112a, 112b, 112c defining a lumen L. IOL 150 is delivered into an eye at the distal end DL of the lumen L. Plunger 140 has a longitudinal axis LA and a soft tip 142 at a distal end of plunger shaft 144. Soft tip 142 is positioned to advance IOL 150 through lumen L to the distal end DL. Soft tip 142 has a concave distal surface C (shown in FIGS. 3A and 3B). IOL 150 comprises an optic body 152 (comprising an imaging portion referred to as an optic) with two or more haptics 154a, 154b extending therefrom for positioning and supporting an optic within the eye into which it is implanted.

Figure 8A:
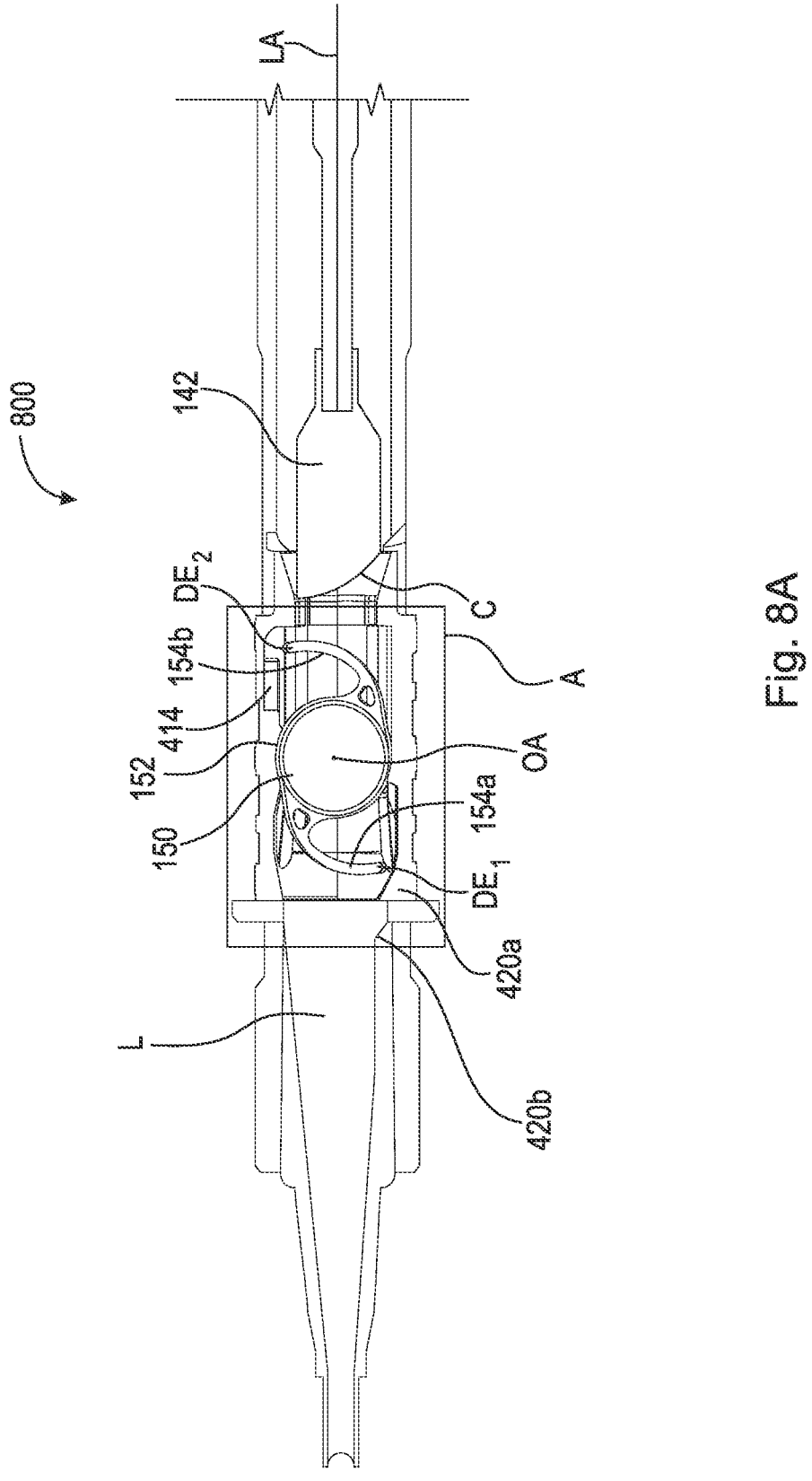
FIG. 8A is a cutaway, schematic top view of the injector body of FIG. 1 having a biased IOL therein, with the plunger actuated to a point where the soft tip is approaching lens.

As will be discussed in greater detail below, concave surface C is configured to facilitate positioning of proximal haptic 154b prior to and/or while the IOL is being compressed and folded, as the IOL progresses down lumen L. According to aspects of the present invention, as shown in FIG. 8A, in a plane including longitudinal axis LA (plane A being perpendicular to the optical axis OA of IOL 150 when the lens is in a staging area of an injector), concave distal surface C extends in a direction at a non-perpendicular angle relative to longitudinal axis LA.). A staging area is the location in an injector where an IOL is located prior to advancement down the lumen by plunger 140.

In the illustrated embodiment, the injector body 102 is comprised of three components (main injector component 110, lens shuttle 120 and cartridge 130) each of which forms a portion of lumen L through which the IOL travels from the staging area to the distal end DL; however, it is to be understood that an injector body may be comprised of one or more components which form the lumen. Also, in the illustrated embodiments, shuttle 120 is comprised of two halves 120a and 120b which snap together or otherwise are coupled together to form the whole shuttle. In the illustrated embodiment, various components of injector system 100 are supported by main injector component 110

Plunger 140 is provided with an actuator 142 to cause plunger 140 to telescope within the injector body and cause the IOL 150 to advance down lumen L. In the illustrated embodiment, finger flanges 114 are formed on the injector body and the actuator is embodied as a thumb press, which in combination facilitate movement of the plunger within the injector body; however, any suitable manual, electromechanical, pneumatic actuator design may be used.

Figures 3A, 3B, 3C:
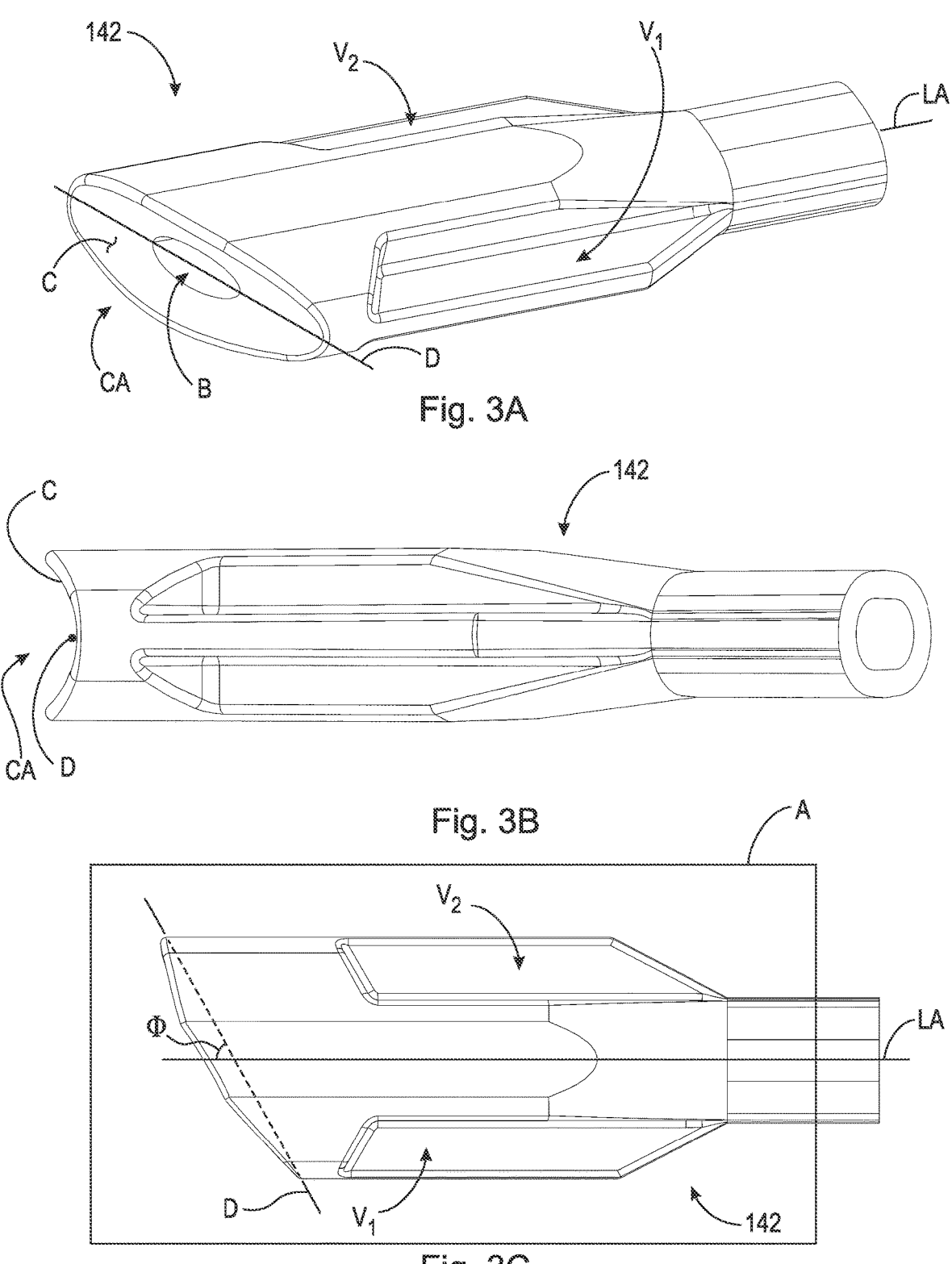
FIG. 3A is a schematic projection view of an example of a plunger soft tip according to aspects of the present invention.
FIG. 3B is a schematic side view taken along direction D of the soft tip shown in FIG. 3A.
FIG. 3C is a schematic top view of the soft tip shown in FIG. 3A.

FIGS. 3A-3C are schematic illustrations of an example of soft tip 142 according to aspects of the present invention. As discussed above, plane A includes longitudinal axis LA, and plane A is perpendicular to optical axis OA of IOL 150 when the lens is in a staging area. In plane A, concave distal surface C extends along a direction D at a non-perpendicular angle 1 relative to longitudinal axis LA. For example, the concave shape can be cylindrical with a circular curvature in a plane perpendicular to an axis extending in direction D and no curvature along an axis extending in direction D; alternatively, the concave shape can have an oval curvature (or another curved shape) perpendicular to an axis extending in direction D and no curvature along an axis extending in direction D. In some embodiments, the distal surface may have a curvature (convex or concave) along direction D in addition to the curvature in the plane perpendicular to direction D.

In planes perpendicular to direction D (at various locations along direction D), the curvature of surface C may be symmetric about direction D or may deviate from symmetric. The orientation of direction D relative to longitudinal axis LA and the remainder of the injector and the IOL is discussed in greater detail, below.

Distal surface C is selected to be concave in planes perpendicular to direction D to facilitate proximal haptic 154b being positioned on top of optic body 152. As discussed in greater detail below with reference to FIGS. 8A-8C, distal surface C is angled relative longitudinal axis LA to cause distal surface C to engage proximal haptic 154b in a manner that causes haptic 154b to bend relative to the optic-haptic connection such that distant end $DE_2$ of the haptic and a portion of the haptic arm A are moved, consistently, to a location on top of optic body 152 rather than compressed into a side of optic body 152.

Soft tip 142 is resiliently deformable so that the soft tip can be compressed as it progresses down lumen L (which has a diminishing cross-section to compress IOL 150) and returns to its original shape once the deformation or compression forces are removed. For example, the soft tip is made of an elastomer (e.g., silicone rubber), a deformable plastic or a deformable thermoplastic. The material is typically a same or lesser hardness as the material of which the IOL is made to avoid damage to the IOL. The material may be a different material or the same material as the IOL 150 to be injected. It is to be appreciated that the concave shape of the soft tip, in combination a lumen shape selected to compress the tip, decreases the likelihood that the proximal haptic or the lens body will become positioned underneath the tip as the tip progress down the lumen. Additionally, as the soft tip progresses down the lumen, the distalmost portions of the soft tip may come together forming a gripping action around the optic body and/or haptic thereby stabilizing the lens as it moved down the lumen.

In some embodiments, distal surface C has no features extending into the concavity CA formed by distal surface C. However, in some embodiments, it has been found beneficial to have a void of material (e.g., a blind bore B) extending through the distal surface and extending proximally through the soft tip from the distal surface, which facilitates compression of the tip as the tip progresses down lumen L. In some embodiments, in planes perpendicular to direction D, (other than in any planes including a blind bore) the distal surface has a continuous curvature.

Voids $V_1$, $V_2$ can be formed in the outer contour of soft tip 142 to facilitate compression of tip 142 and/or, for designs where the soft tip 142 extends beyond distal end DL of the lumen (shown in FIG. 1) as plunger 140 is depressed, to facilitate soft tip 142 re-entering lumen L as the plunger is retracted.

As shown in FIG. 3C, in plane A, concave distal surface C extends in direction D, and direction D extends at a non-perpendicular angle $\Phi$ relative to longitudinal axis LA. Angle $\Phi$ may have a value in the range 40 to 70 degrees; and in some instances, 45 to 65 degrees; for example, and angle of about 60 degrees may be used; where $\Phi$ is specified herein using the acute angle between D and LA; of course, angles between direction D and LA could be specified using an obtuse angle between D and LA that is equivalent to the acute angle specified above. The above angles are representative and can be selected based on the IOL structure (including the haptic or other structure). As discussed in greater detail below with reference to FIG. 8B below, in some embodiments, the plunger begins by contacting less than 10% of the haptic length (as measured from the edge of optic body 152 to the distant end $DE_2$ of the haptic) and typically contacts progressively more of the haptic as the plunger is advanced and the haptic bends. While it is not necessary that the percentage of the haptic that is contacted by the soft tip be non-decreasing as the plunger is advanced, it is typically advantageous that the plunger does not contact more than 50% at any point during the plunger actuation (i.e., up to and including delivery of the IOL through the distal end of the lumen and into an eye).

Figure 4A:
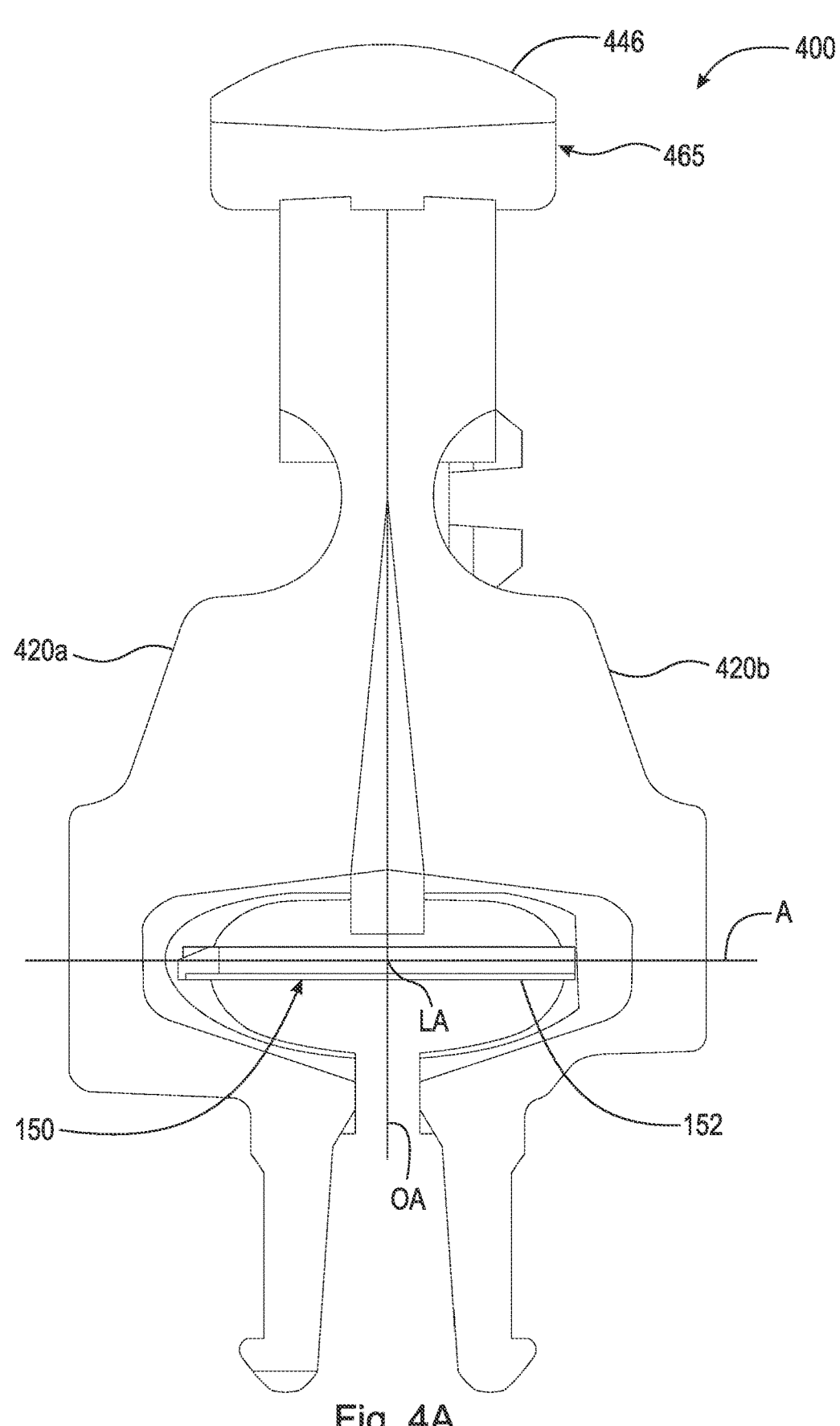
FIGS. 4A-4C illustrate a distal end view, a cutaway side view and a cutaway top view, respectively, of an example of an IOL shuttle in an open position, maintaining a lens in an unbiased state.
Figure 4B:
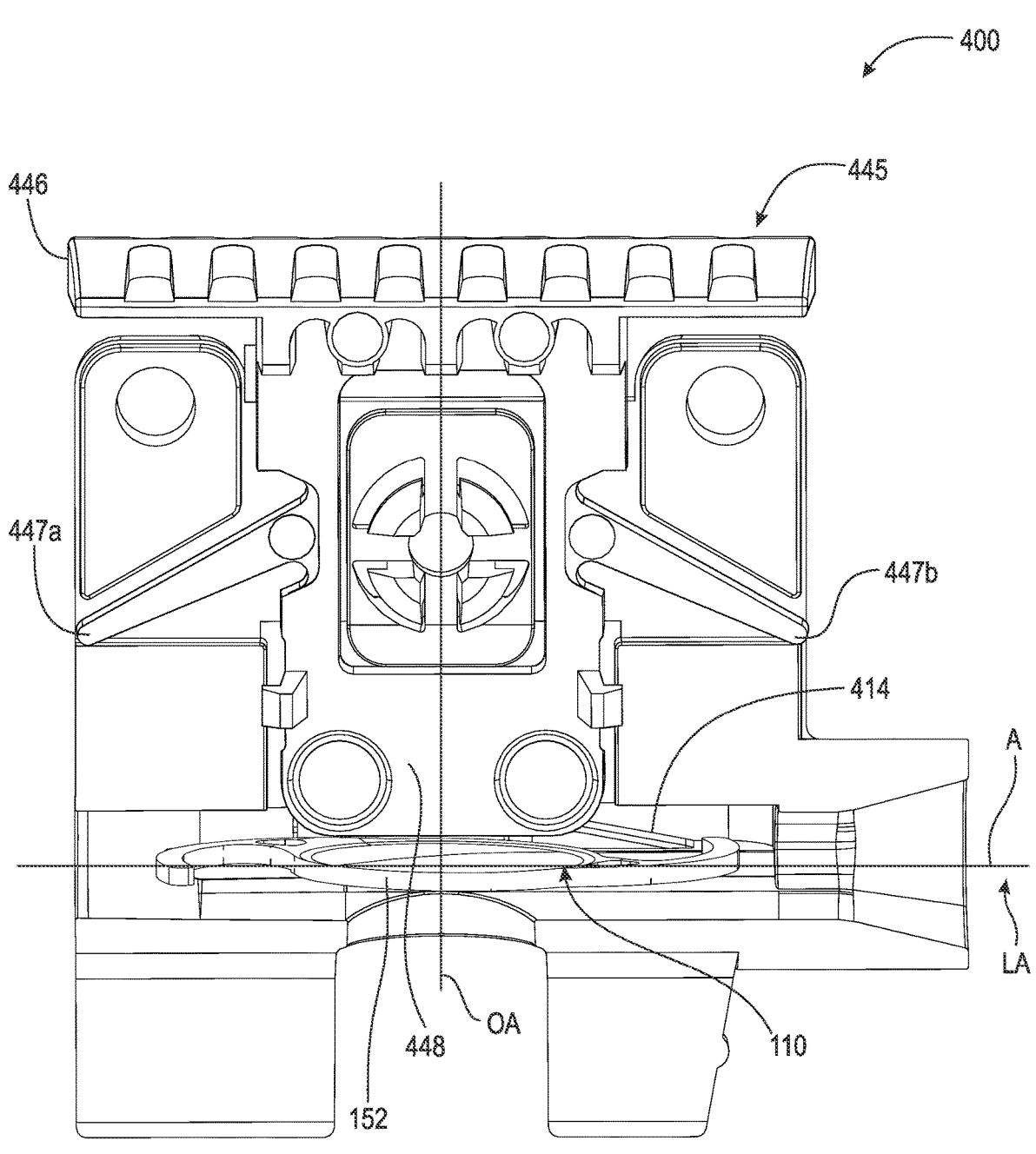
Figure 4C:
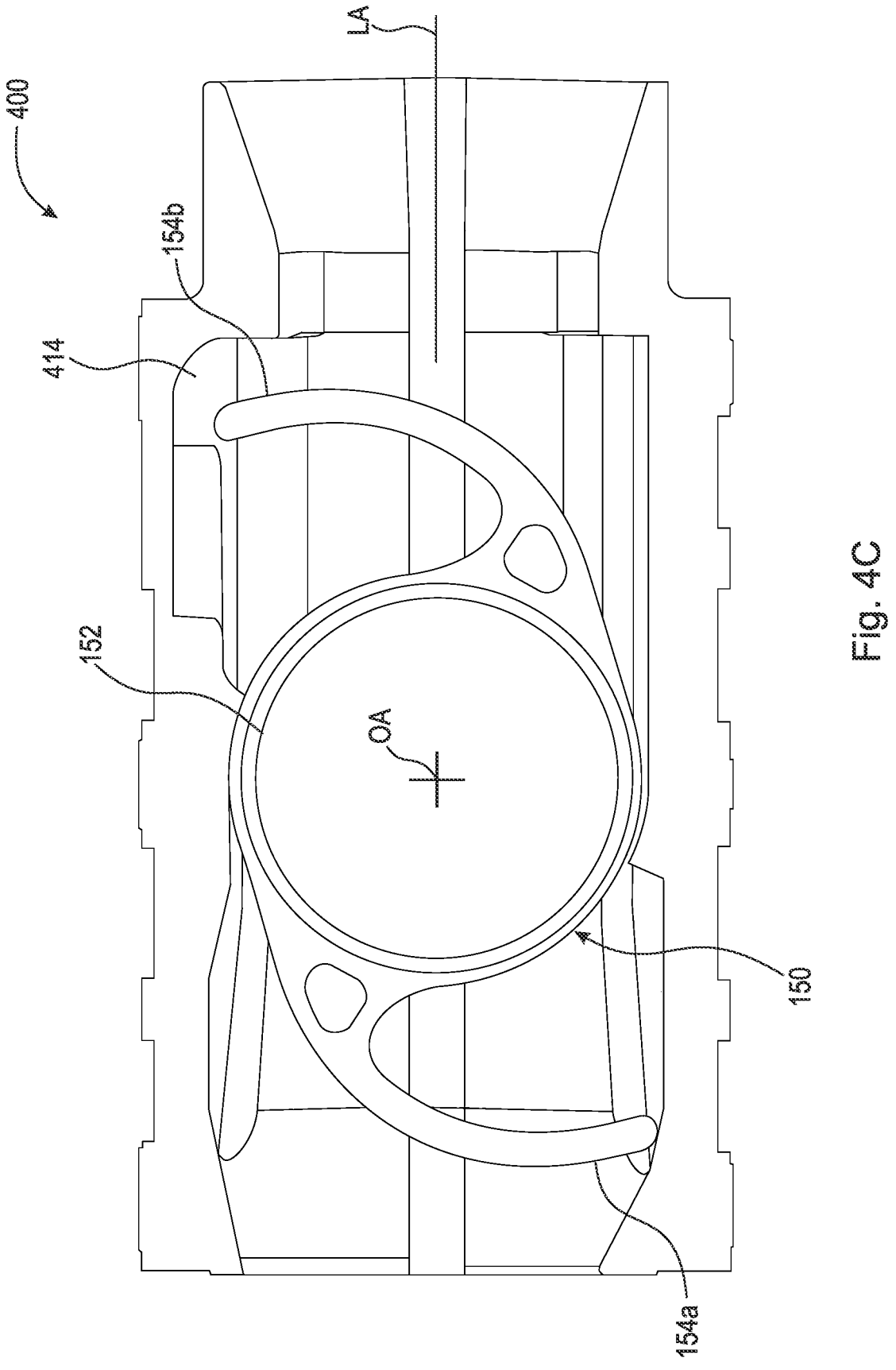

FIGS. 4A-4C illustrate a distal end view, a cutaway side view, and a cutaway top view, respectively, of an example of shuttle 400 (corresponding to shuttle 120 in FIG. 1) in an open position and maintaining an IOL in an unbiased state. (A shuttle and lens so arranged is also referred to as a storage configuration.) By maintaining a lens in an unstressed state, the lens can be stored long-term without affecting the lens's physical and optical characteristics.

In the illustrated embodiment, shuttle 400 comprises a first plate 420a and a second plate 420b which are configured and operate substantially as described in U.S. Pat. No. 11,278,395 issued to Valle et al., the substance of which is incorporated by reference herein in its entirety. Although shuttle 400 is shown as comprising two components, in some embodiments, the shuttle is a single integrated part (FIGS. 7A and 7B), and in other embodiments comprises three or more components.

FIGS. 4A and 4B illustrate edge views of a plane A. Plane A includes longitudinal axis LA and is perpendicular to the lens optical axis OA of an IOL 150 when the IOL is located at a staging area of shuttle 400 and/or injector system 100 (as in FIG. 1).

In the illustrated embodiment of shuttle 400, a biasing tab 445 is included. The biasing tab moves IOL 150 (primarily optic body 152) from a substantially flat shape (i.e., an unbiased state) to a slightly U-shaped shape (also referred to as a smile shape; shown in FIG. 5A), with the center of optic body 152 displaced slightly downward relative to the circumferential outer edge locations of optic body 152 (e.g., such that the optic contacts and may partially conform to lumen wall 412a).

In the embodiment illustrated in FIGS. 4A-4C, as shown in FIG. 4B, biasing tab 445 is positioned to be disposed between first plate 420a and second plate 420b; after connecting components 420a and 420b together, components 420a and 420b maintain biasing tab 445 therebetween. Biasing tab 445 comprises a finger press 446, retraction fingers 447a and 447b and a lens press 448. Operation of the biasing tab is discussed below with reference to FIGS. 5A and 5B. In some embodiments, a ramped surface 414 (also referred to as a ramp) that has a height that increases in the distal direction is added to the side of lumen L such that the distant end $DE_2$ of the haptic 154b rides up the ramp as haptic 154b is advanced down the lumen L toward distal end DL (shown in FIG. 1) further assisting proper positioning of the folded haptic 154b on top of optic body 152.

Figure 5A:
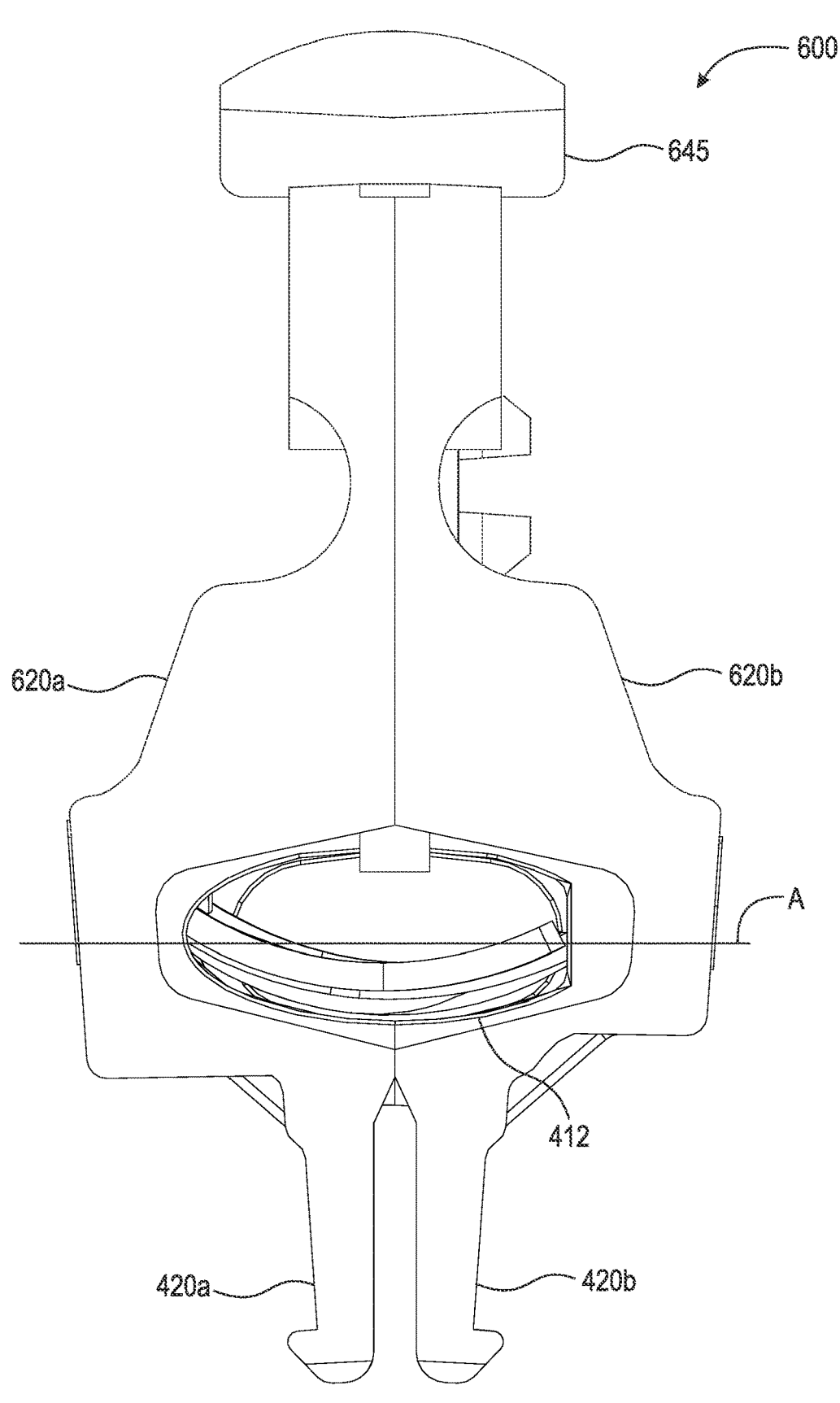
FIGS. 5A-5C illustrate a distal end view, a cutaway side view and a cutaway top view, respectively, of the example of shuttle shown in FIGS. 4A-4C in a closed position maintaining a lens in a biased state.
Figure 5B:
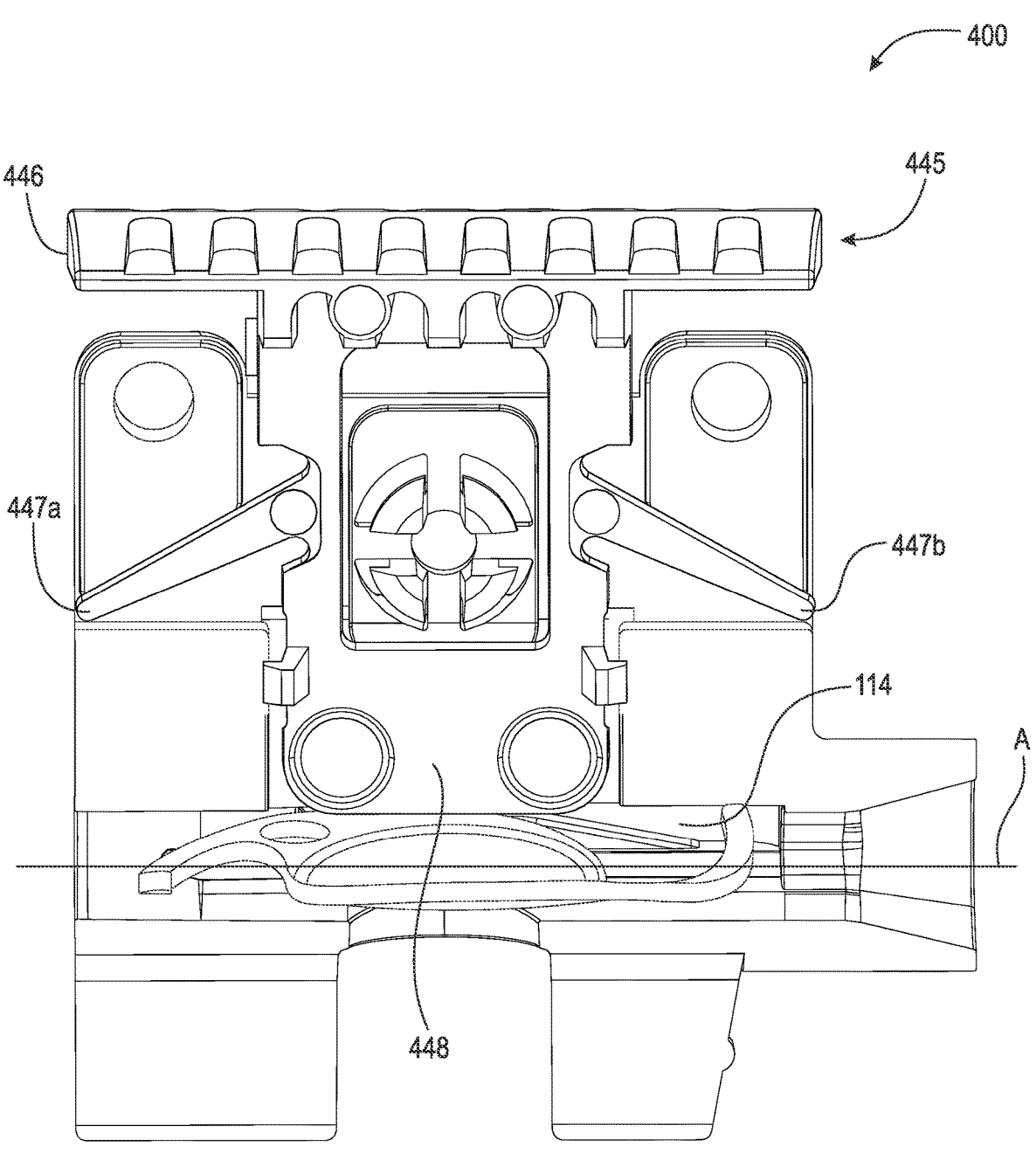
Figure 5C:
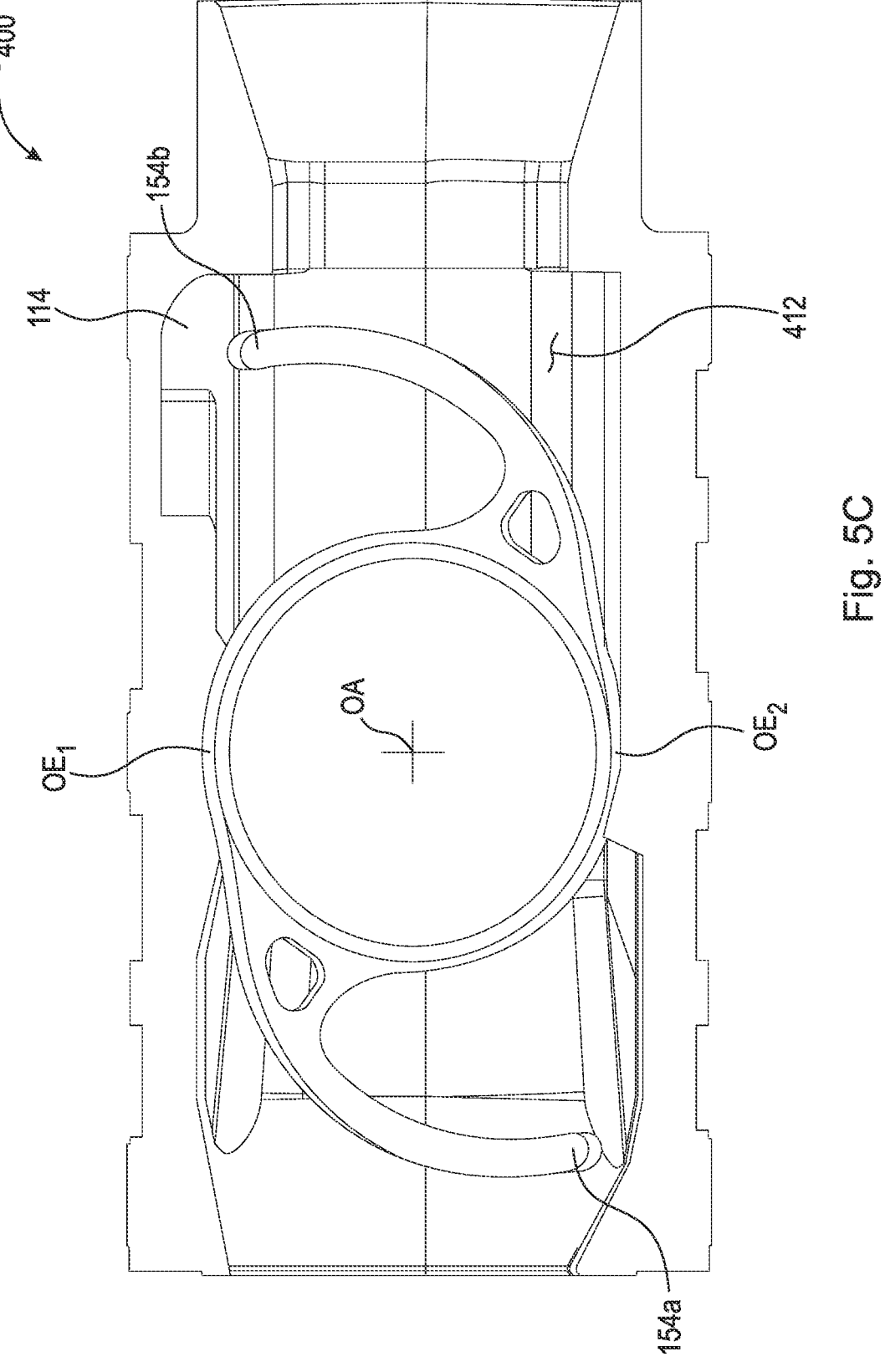

FIGS. 5A-5C illustrate a distal end view, a cutaway side view and a cutaway top view, respectively, of shuttle 400 in a closed position maintaining lens 150 in a biased state.

Closing of the shuttle and maintaining the shuttle in a closed position can be achieved using the retaining tabs 420a, 420b to interact with injector body 110 (shown in FIGS. 1 and 2) as described in U.S. Pat. No. 11,278,395 or may be closed by any other suitable technique. For example, retaining tabs 420a and 420b may be provided with a snapping structure (not shown) such that the retaining tabs snap together by manual operation, without flexure or hinging of the shuttle (e.g., components 420a, 420b) to achieve the closed position.

Regardless of the technique used to close the shuttle 400, as described in U.S. Pat. No. 11,278,395, the interior surfaces of the staging area are moved together, upon closure of the shuttle such that the width dimensions of the lumen are slightly smaller than the outer dimension of the optic body to slightly compress the optic body, and allowing the oval cross-sectional shape of the lumen to cause the optic body to be biased downward.

Figure 6A:
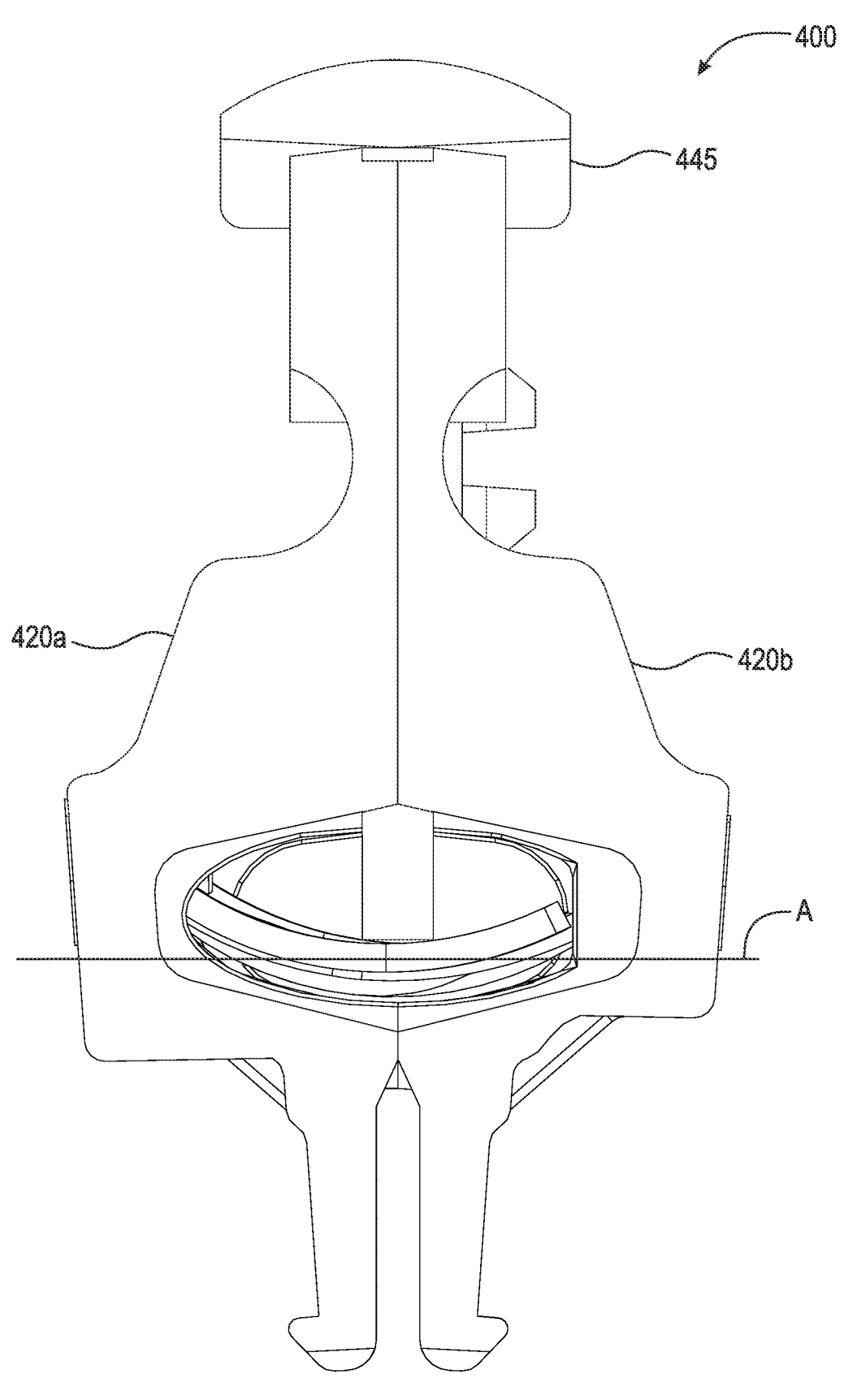
FIG. 6A illustrates a distal end view of the example of a shuttle in FIGS. 4A-4C with the biasing tab depressed to ensure that the lens is in a biased state.
Figure 6B:
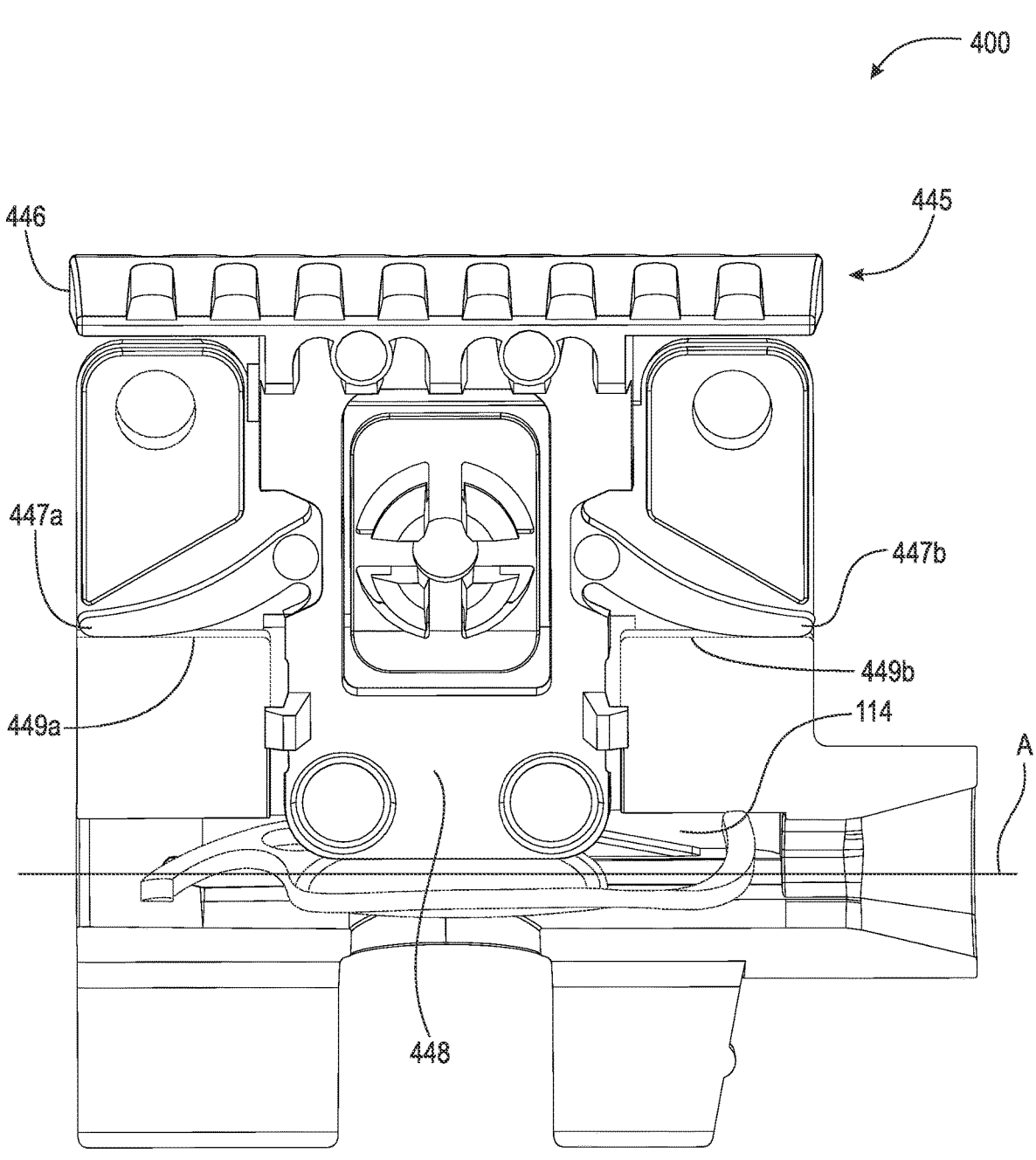
FIG. 6B illustrates a cutaway side view of the shuttle of FIG. 6A with the biasing tab depressed to ensure that the lens is in a biased state and one side of the shuttle omitted for ease of viewing the lens and biasing tab structure.

Although the lumen shape may be selected to achieve biasing of the lens upon closure of the shuttle, biasing tab 445 can be used to ensure that lens is biased downward prior to actuation of the plunger (i.e., a portion of the optic body at optical axis OA is disposed downward relative to opposing circumferential outer edges $OE_1$ and $OE_2$). FIGS. 6A-6B illustrates a distal end view, and a cutaway side view, respectively, of shuttle 400 with biasing tab 445 depressed and lens 150 in a biased state. In FIG. 6A, shuttle 400 is in a configuration with the lumen wall forming a closed circumference (also referred to as a closed state or a loading configuration; illustrated as an oval lumen wall) and with the biasing tab depressed to ensure that the lens in a biased state. As shown in FIG. 6B, as pressure is applied to finger press 446 and biasing tab 445 is depressed, retraction fingers 447a and 447b move outward along landings 449a and 449b, respectively. As pressure on finger press 446 is removed, fingers 447a and 447b move inward along landings 449a and 449b causing lens press 448 to retract. Because optic body 152 is slightly compressed while located in the staging area, pressure on the optic body causes IOL 150 to attain and maintain the smile shape.

Figure 7A:
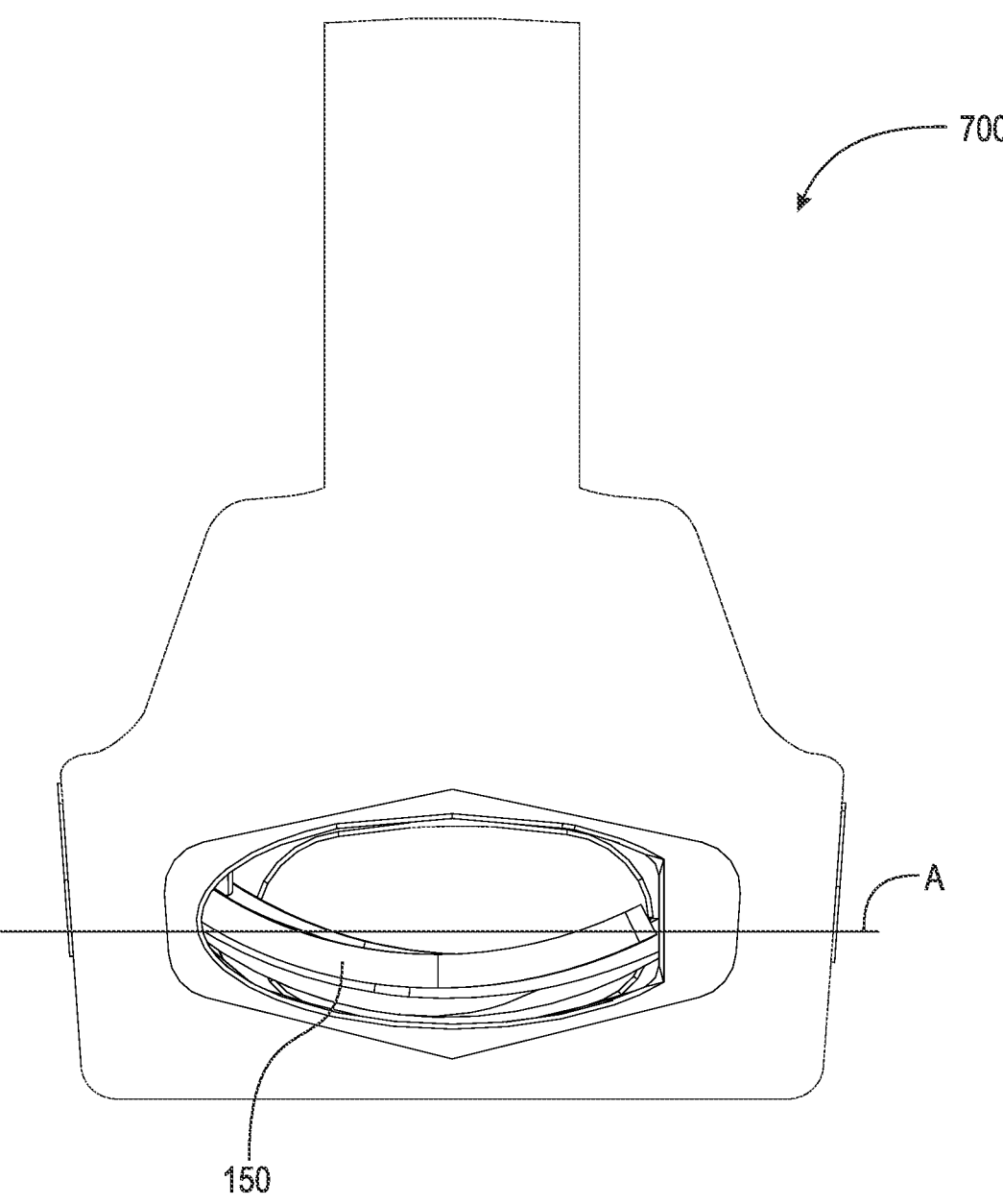
FIGS. 7A-7B illustrate a distal end view and a cutaway top view, respectively, of another example of shuttle.
Figure 7B:
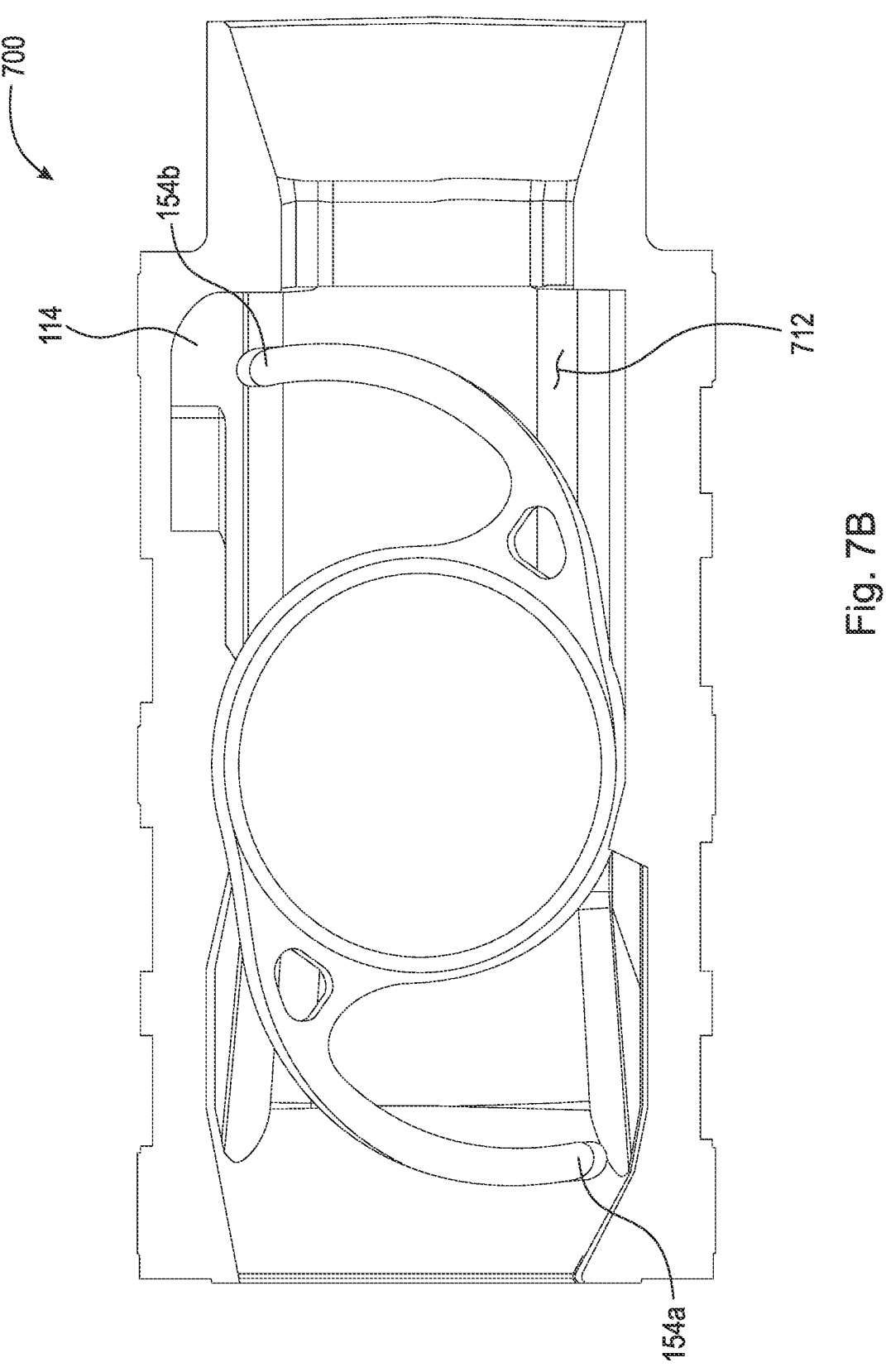

FIGS. 7A-7B illustrate a distal end view and a cutaway top view, respectively, of another example of a shuttle 700. In the illustrated embodiment, shuttle 700 is formed of a single component of rigid construction (i.e., no moving parts, unlike the embodiment described above with reference to FIGS. 4A-4C) or may comprise two or more components to facilitate manufacture or other reasons. FIG. 7A illustrates a distal edge view of a plane A that includes longitudinal axis LA and is perpendicular to the lens optical axis OA of an IOL 150 when the IOL is located at a staging area. Shuttle 700 maintains IOL 150 in a biased state contacting at least a portion of lumen wall 712. Although embodiments above were described as automatically attaining the IOL in the biased state upon closing of the shuttle or upon depressing the biasing tab. In the embodiment shown in FIGS. 7A and 7B, any suitable technique can be used to attain the biased state. For example, biasing may be achieved manually using human fingers or forceps to manipulate the lens to the biased state.

IOL 150 is advanced down lumen L by plunger 140 (shown in FIG. 1) as described above. As described above, a ramp 714 may be present on the side of the lumen corresponding to the free end of proximal haptic 154b, to facilitate placement of the proximal haptic on top of optic, although it is not necessary. Additionally, although the lens is illustrated as being biased while in the staging area, in some embodiments, biasing of a lens in the staging area is not necessary. For example, an oval lumen wall, in combination with the diminishing cross-section of the lumen, can cause center of the optic body (i.e., near the optical axis) to be lower than the sides of the lens (i.e., portions of the lens disposed at the extremes of the oval shape).

FIG. 8A is a cutaway, top schematic illustration of injector body 100 shown in FIG. 1. In FIG. 8A, IOL 150 is in the staging area and plunger 140 is actuated to a point where soft tip 142 is approaching lens 150. For example, the IOL may be an enVista® hydrophobic acrylic IOL from Bausch & Lomb Inc. In FIG. 8A, IOL 150 is not, yet, impacted by soft tip 142.

Figure 8B:
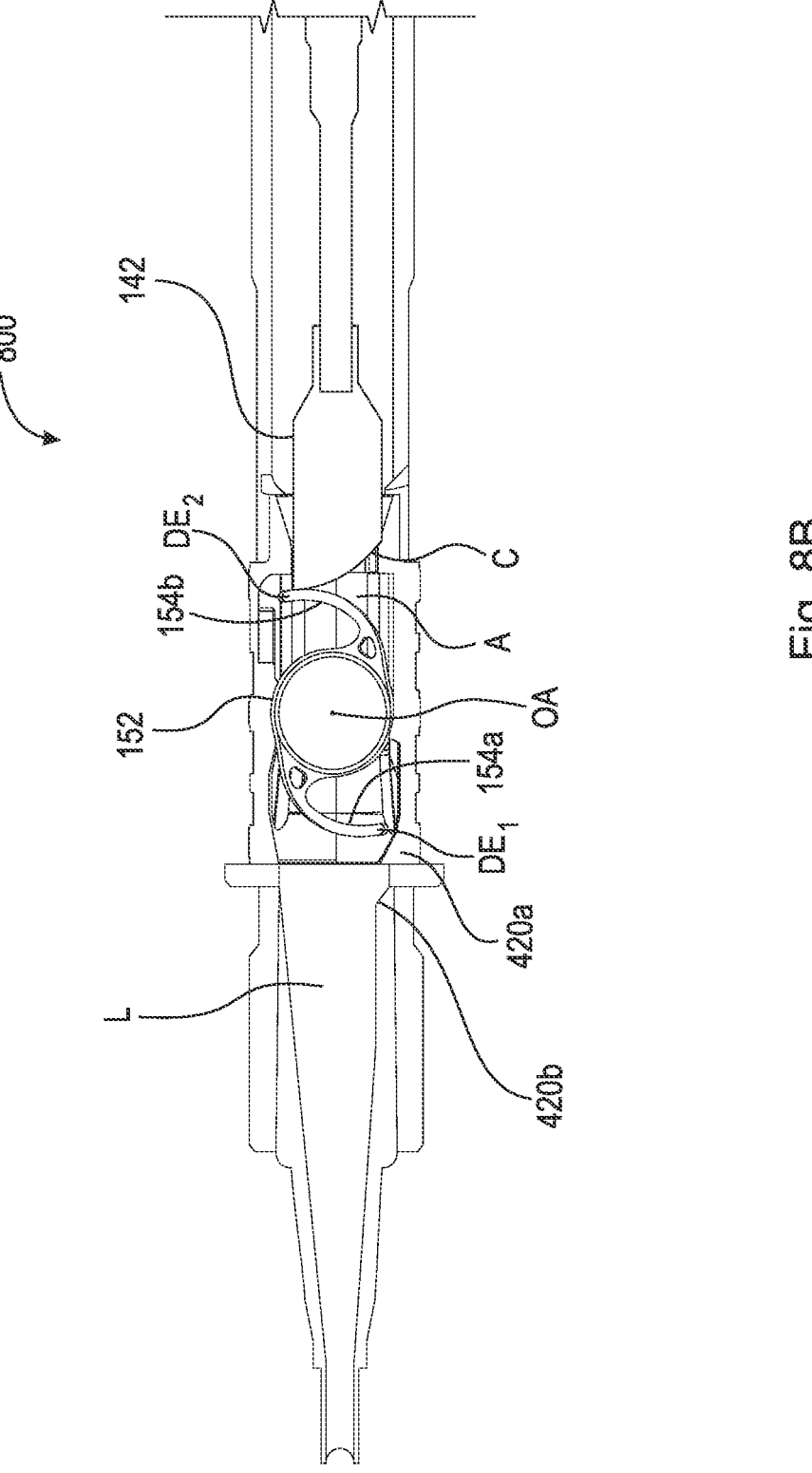
FIG. 8B is a cutaway, schematic top view of the injector body of FIG. 1 of FIG. 1 having a biased IOL therein, with the plunger actuated to a point where the soft tip is making first contact with the lens haptic.

FIG. 8B is a cutaway, top schematic illustration of injector body 100 with plunger 140 actuated to a point where soft tip 142 is making first contact with proximal haptic 154b. In FIG. 8B, it is apparent that soft tip 142 will begin to fold proximal haptic 154b with pressure at a relatively localized position along proximal haptic 154b (e.g., contacting less than 10% of the haptic length). As determined by the inventors, folding proximal haptic 154b with localized pressure along the haptic length (in particular, at the start of the haptic folding process), allows the folding to occur with a decreased likelihood of improper position of the haptic (i.e., compression of the proximal haptic against a side of optic body 152).

Figures 8C, 8D:
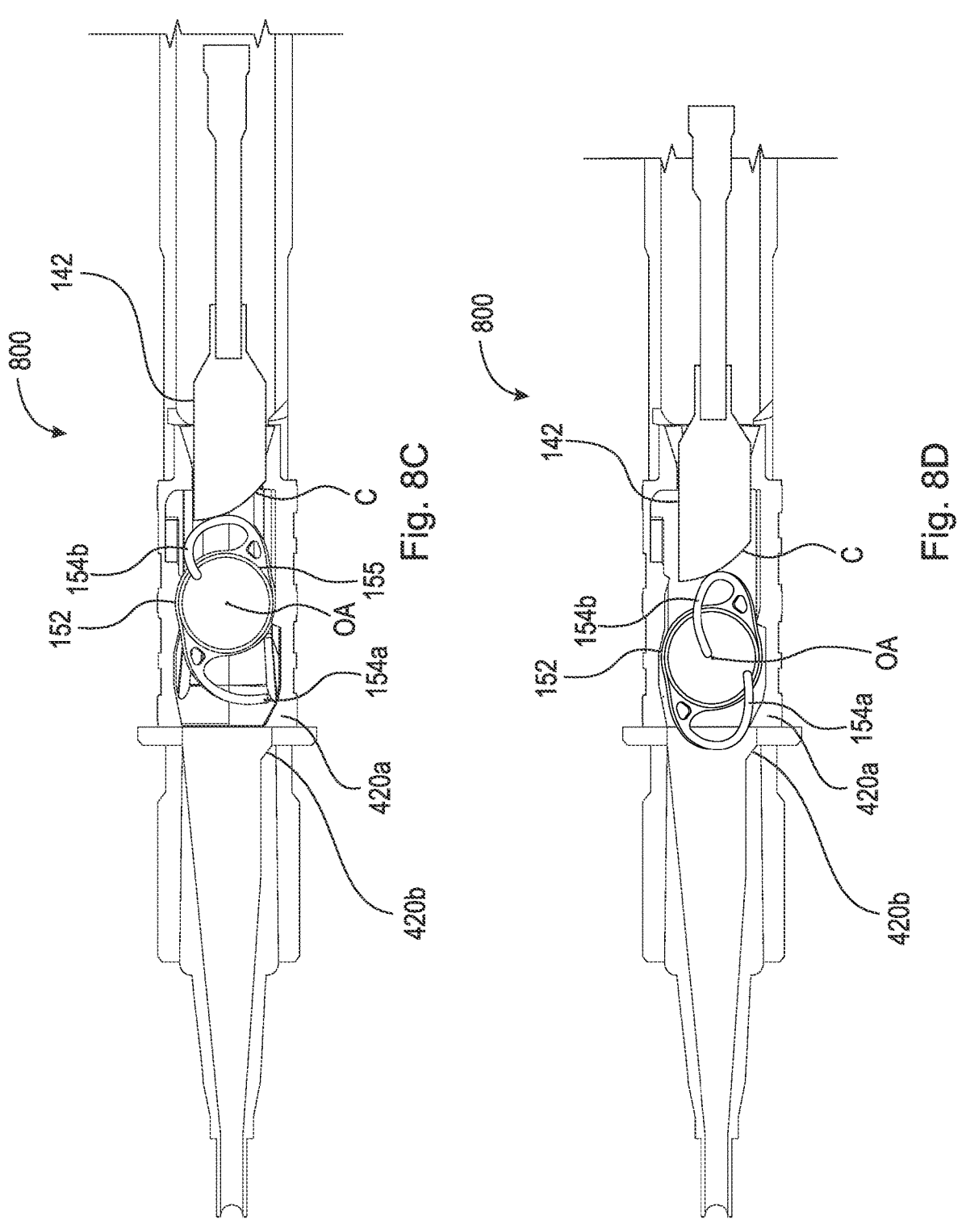
FIG. 8C is a cutaway, schematic top view of the injector body of FIG. 1 having a biased IOL therein, with the plunger actuated to a point where the soft tip is making contact further along the haptic than as shown in FIG. 8B and with plunger contacting a larger portion of trailing haptic (also referred to as proximal haptic) than as shown in FIG. 8B.
FIG. 8D is a cutaway, schematic top view of the injector body of FIG. 1 having a biased IOL therein, with the plunger actuated to a point where the trailing and leading haptics are on top of the lens, and the IOL has begun to advance down the lumen toward the distal end of the lumen.

FIG. 8C is a cutaway, top schematic illustration of the injector body 100, with the plunger 140 making contact further along haptic 154b (i.e., closer to the optic-haptic connection) and plunger 140 contacting a larger portion of haptic 154b. Because haptic folding typically occurs progressively, beginning with a relatively low percentage of the haptic length being contacted and progressing to a large percentage of the haptic length being contacted, folding continues with an increased likelihood that haptic 154b will continue to be positioned on top of optic body 152 and not be compressed against the side of the optic body. Although concave distal surface C and angle 1 in combination with the biasing of optic body 152 (e.g., using biasing tab 445 (shown in FIG. 4A)) increases the likelihood that haptic 154b will be properly positioned on top of optic body 152, in some embodiments, a ramped surface 414 is added to the side of lumen L such that the distant end $DE_2$ of the haptic 154b rides up the ramp as IOL 150 is advanced down the lumen further assisting proper positioning of the folded haptic 154*b* on top of optic body 152.

FIG. 8D is a cutaway, top schematic illustration of the injector body 100, with plunger 140 actuated to a point where soft tip 142 has moved haptic 154*b* on top of optic body 152 in preparation of further compression by the lumen walls.

The diminishing cross-section of the lumen L causes distal haptic 154*a* to be folded toward optic body 152. In some embodiments, it is advantageous if the distal haptic, similar to proximal haptic 154*b* is folded such that the distant end $DE_1$ of the proximal haptic is on top of the optic body as the optic body is compressed. As illustrated, it is typically acceptable if the distal haptic 154*a* is folded to a lesser degree than the proximal haptic 154*b*. In some embodiments, it is advantageous to include one or more haptic restriction elements that impede the progress of a distal portion of the distal haptic relative to the optic body. In the illustrated embodiment, haptic restriction element 420*a* that extends into lumen L to engage the distant end $DE_1$ of the distal haptic 154*a* as the IOL is advanced down the lumen. Haptic restriction element 420*a* is a protuberance extending radially inward from the lumen wall and may has a slope greater than portions of the lumen wall that are adjacent to the restriction element; and haptic restriction element 420*b* is an exposed edge of the haptic wall that has a slope greater than portions of the lumen wall that are adjacent to the restriction element.

Figure 9:
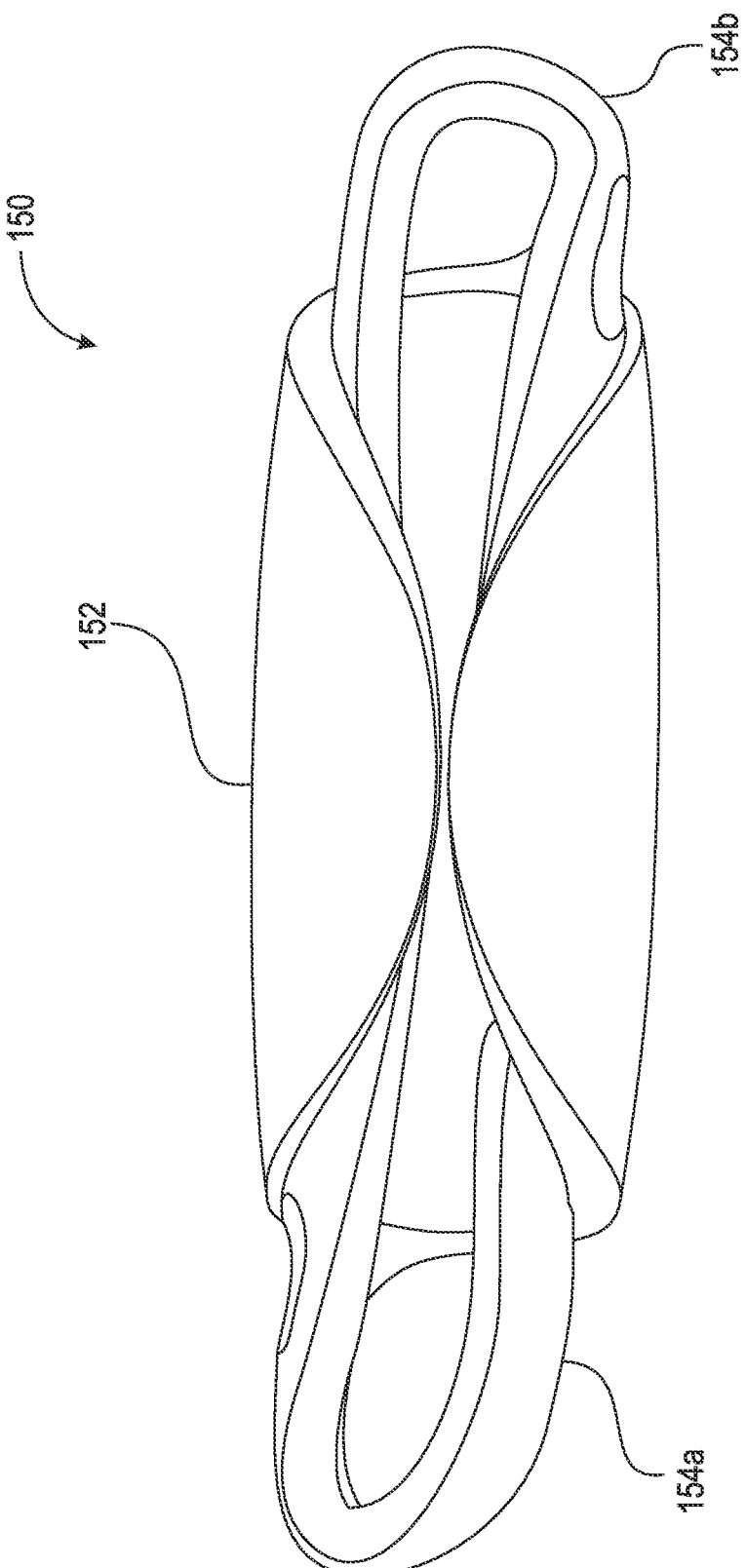
FIG. 9 is a schematic projection illustration of IOL where the distal haptic and the proximal haptic have been folded onto top of optic body according to aspects of the invention.

FIG. 9 is a schematic projection illustration of IOL 150 where the distal haptic 154*a* and the proximal haptic 154*b* have been folded onto top of optic body 152 according to aspects of the invention, as described above; and the sides of the optic body have been rolled toward one another by the lumen wall in a conventional manner, to form what is commonly referred to as a "taco fold". In a taco fold, opposing edges of the optic body may touch one another (as shown), overlap one another, or may be separated from one another. Although in illustrated embodiment the lens as it emerges from the distal end of the lumen has a taco fold, a plunger as described herein may be used with any suitable technique for folding an optic body.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An injector system for injecting an intraocular lens (IOL) into an eye, comprising:
    an injector body having a lumen wall defining a lumen, the lumen having a distal end configured to permit the IOL to be delivered into the eye; and
    a plunger having a longitudinal axis and a soft tip at a distal end of the plunger, the soft tip being configured to advance the IOL through the lumen to the distal end of the lumen, the soft tip having a concave distal surface with a plane extending therethrough,
    the plane including the longitudinal axis and the plane being perpendicular to an IOL optical axis when the IOL is located at a staging area of the injector body, and in the plane, the concave distal surface extending in a direction at a non-perpendicular angle relative to the longitudinal axis, the direction being tangential to the concave distal surface along its length.

2. The injector system of claim 1, wherein the concave distal surface is oval-shaped in a plane perpendicular to the direction.

3. The injector system of claim 1, wherein the concave distal surface is circularly cylindrically-shaped in a plane perpendicular to the direction.

4. The injector system of claim 1, wherein the soft tip comprises an elastomer.

5. The injector system of claim 1, wherein the concave distal surface defines a concavity and wherein no feature of the soft tip extends into the concavity.

6. The injector system of claim 1, wherein the concave distal surface has a blind bore formed therethrough, the blind bore extending through the soft tip proximally from the concave distal surface.

7. The injector system of claim 1, wherein the angle is in the range of 40-70 degrees.

8. The injector system of claim 1, wherein the angle is in the range of 45-65 degrees.

9. The injector system of claim 1, wherein the angle is about 60 degrees.

10. The injector system of claim 1, having an IOL disposed in a staging area of the injector body, the IOL having a haptic extending proximally from the optic, the soft tip configured to contact less than 10% of the haptic length as measured from the optic body to a distant end of the haptic, at initial contact between the soft tip and the haptic.

11. The injector system of claim 10, wherein the soft tip is configured to contact no more than 50% of the haptic length at any point during the plunger actuation.

12. The injector system of claim 1, wherein the injector body is comprised of two or more components each forming a portion of the lumen.

13. The injector system of claim 12, wherein at least one of the components constitutes an IOL shuttle.

14. The injector system of claim 13, wherein the shuttle has an IOL disposed therein in a biased state with a center of an optic body displaced relative to opposing circumferential outer edge locations of the optic body such that the optic body contacts and conforms to a wall of the lumen.

15. A method of inserting an intraocular lens (IOL) including an optic body and a haptic into an eye by operating the injector system of claim 1, the method comprising:
    inserting the IOL at the staging area; actuating the plunger to move a portion of the haptic on top of the optic body.

16. The method of claim 15, wherein the actuating step comprises, upon initial contact with the haptic, contacting less than 10% of the haptic length as measured from the optic body to a distant end of the haptic.

17. The method of claim 15, wherein the actuating step comprises, moving the IOL from a staging area of the injector body through a distal end of the lumen while contacting no more than 50% of the haptic length at any point during movement of the IOL from the staging area to the distal end of the lumen.

18. The method of claim 15, wherein the concave distal surface is oval-shaped in a plane perpendicular to the direction.

* * * * *